US010376667B2

(12) United States Patent
Peets

(10) Patent No.: US 10,376,667 B2
(45) Date of Patent: Aug. 13, 2019

(54) INTRANASAL AIRWAY DEVICE

(71) Applicant: Ronald Peets, Sun City Center, FL (US)

(72) Inventor: Ronald Peets, Sun City Center, FL (US)

( * ) Notice: Subject to any disclaimer, the term of this patent is extended or adjusted under 35 U.S.C. 154(b) by 0 days.

(21) Appl. No.: 15/595,160

(22) Filed: May 15, 2017

(65) Prior Publication Data

US 2017/0246413 A1    Aug. 31, 2017

Related U.S. Application Data

(63) Continuation-in-part of application No. 14/299,209, filed on Jun. 9, 2014, now abandoned.

(51) Int. Cl.
*A61M 15/08* (2006.01)
*A61M 16/06* (2006.01)
*A61M 16/08* (2006.01)
*A61M 16/10* (2006.01)

(52) U.S. Cl.
CPC ...... *A61M 16/0666* (2013.01); *A61M 15/085* (2014.02); *A61M 16/0672* (2014.02); *A61M 16/0816* (2013.01); *A61M 16/10* (2013.01); *A61M 2202/0208* (2013.01)

(58) Field of Classification Search
CPC .......... A61M 16/0672; A61M 16/0666; A61M 16/0816; A61M 2202/0208; A61M 16/10; A61F 5/08; A62B 23/06
See application file for complete search history.

(56) References Cited

U.S. PATENT DOCUMENTS

| | | | | |
|---|---|---|---|---|
| D89,947 S | * | 5/1933 | Cohn | D24/106 |
| 2,046,664 A | * | 7/1936 | Weaver | A62B 23/06 128/206.11 |
| 2,162,583 A | * | 6/1939 | Kjellsson | A62B 23/06 128/206.11 |
| 2,672,138 A | * | 3/1954 | Carlock | A61F 5/56 128/206.11 |
| 2,715,401 A | * | 8/1955 | Appel | A62B 23/06 128/206.11 |
| 3,513,839 A | * | 5/1970 | Vacante | A62B 23/06 128/204.12 |
| 3,747,597 A | * | 7/1973 | Olivera | A62B 23/06 128/206.11 |
| 3,902,486 A | * | 9/1975 | Guichard | A61M 15/00 128/203.22 |
| 4,201,217 A | * | 5/1980 | Slater | A61F 5/56 606/199 |
| 4,273,124 A | * | 6/1981 | Zimmerman | A61M 16/0666 128/207.18 |
| 4,327,719 A | * | 5/1982 | Childers | A62B 23/06 128/203.22 |

(Continued)

*Primary Examiner* — Gregory A Anderson
*Assistant Examiner* — Victoria Murphy
(74) *Attorney, Agent, or Firm* — Thomas VanZandt

(57) ABSTRACT

An intranasal device having a first cannula for insertion into a first nostril of a user and a second cannula for insertion into a second nostril of a user. Each cannula has an interior surface defining a generally cylindrical lumen. On the exterior surface of each cannula is a first protrusion in the shape of an anteromedial concavity of a nostril of the user and second, separate and distinct protrusion in the shape of a posterolateral concavity of the nostril of the user.

5 Claims, 4 Drawing Sheets

(56) References Cited

U.S. PATENT DOCUMENTS

| | | | | |
|---|---|---|---|---|
| 4,648,398 A * | 3/1987 | Agdanowski | A61M 16/0666 | 128/207.18 |
| 5,105,807 A * | 4/1992 | Kahn | A61M 25/02 | 128/200.26 |
| 5,117,820 A * | 6/1992 | Robitaille | A62B 23/06 | 128/201.18 |
| 5,425,359 A * | 6/1995 | Liou | A62B 23/06 | 128/206.11 |
| 5,595,174 A * | 1/1997 | Gwaltney | A61M 16/0666 | 128/201.13 |
| 5,890,491 A * | 4/1999 | Rimkus | A62B 23/06 | 128/204.12 |
| 6,004,342 A * | 12/1999 | Filis | A61F 5/08 | 606/199 |
| 6,386,197 B1 * | 5/2002 | Miller | A61F 5/08 | 128/200.24 |
| 6,484,725 B1 * | 11/2002 | Chi | A63B 33/00 | 128/858 |
| 6,561,188 B1 * | 5/2003 | Ellis | A61M 3/0262 | 128/203.22 |
| 6,564,800 B1 * | 5/2003 | Olivares | A61F 5/08 | 128/200.24 |
| 6,705,315 B2 * | 3/2004 | Sullivan | A61B 5/097 | 128/204.18 |
| 7,080,645 B2 * | 7/2006 | Genger | A61M 16/00 | 128/204.18 |
| D576,726 S * | 9/2008 | Maxwell | D24/106 | |
| 8,225,796 B2 * | 7/2012 | Davenport | A61B 5/087 | 128/207.18 |
| 8,322,340 B2 * | 12/2012 | Talmon | A62B 23/06 | 128/206.11 |
| 8,833,369 B2 * | 9/2014 | Dolezal | A61M 15/08 | 128/206.11 |
| D737,965 S * | 9/2015 | Bende | D24/135 | |
| 2002/0046755 A1 * | 4/2002 | De Voss | A61M 16/0666 | 128/207.18 |
| 2004/0055603 A1 * | 3/2004 | Bruce | A62B 23/06 | 128/206.11 |
| 2004/0065065 A1 * | 4/2004 | Van Patten | A62B 23/06 | 55/385.1 |
| 2004/0211425 A1 * | 10/2004 | Wang | A61M 15/00 | 128/206.11 |
| 2005/0161049 A1 * | 7/2005 | Wright | A61M 16/0666 | 128/207.18 |
| 2005/0211254 A1 * | 9/2005 | Olson | A61F 11/08 | 128/864 |
| 2006/0174889 A1 * | 8/2006 | Noble | A61M 16/01 | 128/206.11 |
| 2007/0088334 A1 * | 4/2007 | Hillis | A61B 5/0002 | 604/891.1 |
| 2007/0106321 A1 * | 5/2007 | Funabashi | A61F 5/08 | 606/196 |
| 2007/0106382 A1 * | 5/2007 | Tohara | A62B 23/06 | 623/10 |
| 2008/0009897 A1 * | 1/2008 | Duran Von Arx | A61F 5/08 | 606/199 |
| 2008/0015540 A1 * | 1/2008 | Muni | A61B 17/24 | 604/500 |
| 2009/0020125 A1 * | 1/2009 | Chang | A62B 23/06 | 128/206.11 |
| 2009/0093840 A1 * | 4/2009 | MacDonald | A61F 5/08 | 606/199 |
| 2009/0250067 A1 * | 10/2009 | Beck Arnon | A61M 15/08 | 128/207.18 |
| 2009/0272386 A1 * | 11/2009 | Kurtz | A61F 5/56 | 128/848 |
| 2010/0229872 A1 * | 9/2010 | Ho | A61M 16/06 | 128/206.25 |
| 2010/0331777 A1 * | 12/2010 | Danielsson | A61F 5/08 | 604/104 |
| 2012/0125340 A1 * | 5/2012 | Chou | A61M 16/105 | 128/206.11 |
| 2013/0081637 A1 * | 4/2013 | Foley | A61F 5/08 | 128/848 |
| 2014/0246023 A1 * | 9/2014 | Maryanka | A61F 5/08 | 128/203.22 |
| 2014/0326244 A1 * | 11/2014 | Orts Paya | A62B 23/06 | 128/206.11 |
| 2015/0136139 A1 * | 5/2015 | Franzen | A61M 16/0622 | 128/205.25 |

\* cited by examiner

INTRANASAL AIRWAY DEVICE

CLAIM OF PRIORITY

This application claims priority from U.S. patent application Ser. No. 14/299,209 which claims priority from U.S. Provisional Patent Application No. 61/832,858, entitled "Intranasal Airway Device", filed on Jun. 9, 2013.

FIELD

Embodiments of the invention relate generally to the field of nasal obstructions, and more specifically to a nasal airway device for reducing impediments to nasal airflow thereby reducing negative inhalation pressure in the body's airway.

BACKGROUND

Since human noses have a limited range of sizes and anatomical detail, typical intranasal airway (INA) devices are similar in size and conformity. Such devices may be used to increase nasal airflow, for filtering air, delivering medication, and for swimming Typical INA devices include a pair of cannulae having a cylindrical or frustoconical shape and may include filters, valves, hoses, etc.

Conventional INA devices have many disadvantages. One disadvantage is the insertion and removal of the INA device. For example, a cylindrical INA device may be more difficult to insert and more difficult to insert farther into the nasal passage, and, while a frustoconical INA device may be inserted easier and farther, it is at the expense of decreased airflow. Also, conventional INA devices are typically removed by pulling on a connecting portion that connects the cannulae. This is often uncomfortable as it drags the cannulae against the septum.

Another disadvantage is that INA devices, whether cylindrically or frustoconically shaped, are difficult to retain in place due to nasal mucous and the pressure of exhalation. Additionally, INA devices are typically manufactured to have some mechanism for maintaining their shape during use. This may include manufacture from a rigid or semi-rigid material or a rigid support inserted or integrated with a pliable material. Such mechanisms, while helping to maintain the shape of the INA device and helping maintain increased airflow, also increase the propensity of the INA device to become unintentionally dislodged from the nasal passage.

Some conventional INA devices address the problem of device retention through use of an external retention device such as a strap or clip that holds the INA device to the user's head or nose. Such retention devices (e.g., retention strap) are uncomfortable and interfere with the user's activities. Moreover, some external retention devices (e.g., retention clip) decrease airflow.

Another conventional method of addressing device retention is to form a protrusion on the outer surface of the cannulae of the device. For some conventional devices, such protrusions are directed toward the septum such that the protrusions on each cannula form a retaining clamp on the septum. Although, this helps to retain the INA device, it decreases airflow. Airflow is decreased because the protrusion causes a narrowing of the nasal passage, blocks a portion of the nasal passage used for airflow, and directs the aperture of each cannula inward, inhibiting airflow through the device to the nasal passage.

For other conventional devices, the retaining protrusions are directed away from the septum and toward the inner surface of the lateral portions of the nose. Again, while this protrusion scheme helps to retain the INA device, it decreases airflow by blocking a portion of the nasal passage used for airflow, and directing the aperture of each cannula outward toward the inner surface of the lateral portions of the nose which likewise inhibits airflow through the device to the nasal passage.

Another distinct disadvantage of conventional INA devises is that in attempting to promote their desired use of nasal airflow and promote device retention the device instead causes a degree of obstruction of the nasal passage resulting in decreased airflow by increasing the negative inhalation pressure which narrows the lumen of the nasal airways. The inclusion of such parts and retention protrusions compromise the lumen, thus resulting in reduced airflow. Some devices have a rim around the cannula. The rim is a uniform protrusion from the cannula with a generally annular shape. When pushed into the nostril the rim catches on the nasal concavities. Part of the rim will go into the anteromedial concavity and posterolateral concavity and the remainder of the rim will be pressed against the other portions of the interior of the nostril. See U.S. Pat. No. 8,833,369 to Dolezal, et al. While these devices provide device retention, because the rim is caught in the nostril, they provide only limited reduction of airflow impediments. Because the rim is of a general and uniform shape around the entire cannula the rim obstructs the nostril. Such devices increase the pressure against some portions of the nostril in an unnecessary and irritating manner Such pressure may reduce, rather than increase, airflow.

Other conventional devices may include a sponge-like seal that protrudes from the cannula. The seal is uniform around the cannula. This seal is compressible and when pushed into the nostril the compressible material expands to some degree into the anteromedial concavity and the posterolateral concavity and the remainder will remain compressed or become even more compressed as it is pressed against the other portions of the interior of the nostril. See U.S. Pat. No. 4,648,398 to Agdanowski, et al. The compressible material will expand to fill some areas of the nostril, depending on how far the device is inserted. But again, because of the uniform distribution of the compressible material prior to insertion, there will be uneven pressure against the nostril which may be irritating and may decrease airflow.

A distinct and major disadvantage of all prior art devices is that they fail to address the problems that arise when the nostrils, for various reasons are inadequate for the prevailing required airflow. Under such circumstances, a progressive accumulation of excessive negative inhalation pressure may occur. This may cause narrowing of the body's compliant airway. The increased negative pressure narrows the compliant airway and reduces nasal airflow. The restricted flow of ambient air may cause the user to inhale more forcefully and enter a cycle of increased negative inhalation pressure with an increase of the partial vacuum pressure on the compliant portions of the nasal passage which may decrease the level of available oxygen.

SUMMARY

An intranasal airway device having two cannulae connected by a connecting portion. Each cannula has an approximately cylindrically shaped lumen. Each lumen has a diameter throughout its length, which diameter, depending upon the size of the device, ranges from approximately 7 mm to 15 mm The outer surface of each cannula has one or more anatomically conforming protrusions. Conforming, as used here, means having a similar form, and each cannula has protrusions that have the shape of the human nasal concavities located anteromedially and posterolaterally in all normally developed human nostrils. One aspect of the inventive concept disclosed in this application is that the human nasal cavity has a particular shape within some minor variance, and that this particular shape is common to almost all human nasal cavities. The term nareiform (nă-rā-ə-fôrm) will be used herein to describe this particular shape. For one embodiment of the invention the design features reduce impediments to the flow of ambient air at ambient pressure. For one such embodiment, the design features reduce the likelihood of typical negative inspiratory pressure progressing to the point of constricting the body's airway. Such an embodiment, therefore, reduces the likelihood that the user will experience oxygen deprivation.

For one embodiment of the invention, the outer surface of each cannula has two anatomically conforming protrusions that project toward the anatomical cul-de-sac concavities inside the nostrils to engage the anteromedial and posterolateral cul-de-sac concavities, which are consistent characteristics of the typical human nose. The anatomically conforming protrusions support the nostrils in a wide-open posture and provide increased airflow relative to prior art designs, while providing device retention and positioning.

For one embodiment of the invention, each cannula has a first anatomically conforming protrusion and a second anatomically conforming protrusion. The first anatomically conforming protrusion is directed anteriorly to engage the anteromedial concave recess of the nostril. The second anatomically conforming protrusion is directed posteriorly and somewhat laterally away from the septum to engage the posterolateral recess of the nostril. The anatomically conforming protrusions project outwardly from the exterior of the cannulae in a plane that is approximately perpendicular to the centerline of the lumeni and the nasal septum and approximately parallel to the base of the device. For one such embodiment, each cannula further includes a relatively small protrusion directed toward the nasal septum.

Embodiments of the invention help to lessen the buildup of negative inspiratory pressure in the body's air passageway to the lungs. The buildup of negative inspiratory pressure narrows that compliant passageway, further increasing inspiratory effort in a crescendo cycle which may cause hypoxia.

Embodiments of the invention overcome the prior art disadvantages associated with space-occupying extraneous parts that impede nasal airflow. Embodiments of the invention hold the nostrils open wider, while positioning the retaining elements of the device in the nasal concavities and out of the path of natural airflow. For some embodiments, the cannulae are sufficiently flexible to allow insertion into the nostrils, while sufficiently resilient to support the soft sides of the nostrils cephalad to the nostril's flared rim. This allows the nostril to be held in a wide-open positon while reducing or elimination points of pressure within the nasal cavity.

BRIEF DESCRIPTION OF THE DRAWINGS

The foregoing summary, as well as the following detailed description of preferred embodiments, is better understood when read in conjunction with the appended drawings. For the purpose of illustrating the invention, there is shown in the drawings exemplary constructions of the invention; however, the invention is not limited to the specific methods and instrumentalities disclosed. In the figures of the accompanying drawings like reference numerals refer to similar elements. In the drawings.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

Reference throughout the specification to "one embodiment" or "an embodiment" means that a particular feature, structure, or characteristic described in connection with the embodiment is included in at least one embodiment of the present invention. Thus, the appearance of the phrases "in one embodiment" or "in an embodiment" in various places throughout the specification are not necessarily all referring to the same embodiment. Furthermore, the particular features, structures, or characteristics may be combined in any suitable manner in one or more embodiments.

Moreover, inventive aspects lie in less than all features of a single disclosed embodiment. Thus, the claims following the Detailed Description are hereby expressly incorporated into this Detailed Description, with each claim standing on its own as a separate embodiment of this invention.

Embodiments of the invention are applicable in a variety of settings in which increased or improved nasal airflow is desired.

Figure 1:
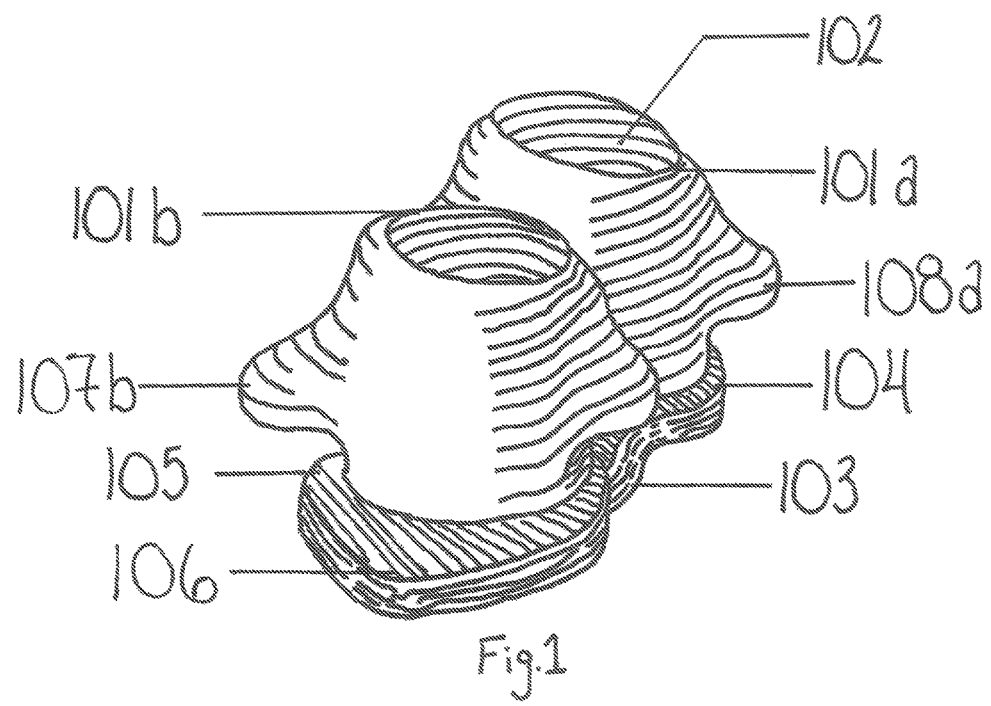
FIG. 1 illustrates an intranasal airway device in accordance with one embodiment of the invention.

FIG. 1, illustrates an intranasal airflow (INA) device in accordance with one embodiment of the invention. As shown in FIG. 1, the INA device includes cannula 101a and cannula 102b that are open at both an insertion end 102 and an exterior end (not shown). The lumen of the cannulae 101a and 102b have an approximately uniform diameter throughout their length. The interior of the cannulae is substantially cylindrically shaped. For various embodiments, the lumeni range in size from approximately 7 mm to 14 mm The cannulae range in length from approximately 1.2 cm to 2.6 cm for various embodiments. The cannulae are connected to each other by a connecting portion (bridge) 103. The connecting portion separates the cannula a distance of approximately 4 mm to 12 mm depending on the size of the device for various embodiments. For one embodiment, each cannula has a base, shown, for example as base 104. The base supports the cannula and may include anterior flanges 105 and lateral flanges 106. For one embodiment, the interior flanges 105 and lateral flanges 106 may be used to hold and manipulate the INA device during insertion or removal, or to adjust the INA device during use. Each of the cannula may include anatomically conforming protrusions, shown, for example, as anatomically conforming protrusions 107b and 108a.

As shown in FIG. 1, the anatomically conforming protrusion 107b is directed anteriorly to engage the anteromedial concave recess of the nostril (not shown) and the anatomically conforming protrusion 108a is directed posteriorly and laterally to engage the posterolateral recess of the nostril. The anatomically conforming protrusions project outwardly from the exterior of the cannulae in a plane that is approximately perpendicular to the centerline of the lumeni and the nasal septum and approximately parallel to the base of the device. The distinct shape of each cannula of the INA device, as shown in FIG. 1, is termed nareiform and is the shape of the human nostril. The INA device as shown in FIG. 1 is contoured to be inserted into a respective nostril. As shown in FIG. 1, the cannulae 101a and 102b of the INA device do not have a uniform lip or protrusion around the entire surface, but rather each cannula has two distinct protrusions 107b and 108a that correspond to and mate with the anteromedial concave recess of the nostril and the posterolateral recess of the nostril, respectively. Also, the two distinct and separate protrusions 107b and 108a have different dimensions and may not be the same distance from the base 104, as described further below in reference to FIG. 3. The dimensions are different because the anteromedial concave recess of the nostril and the posterolateral recess of the nostril have different dimensions. The cannulae of the INA device are produced with this distinct nareiform shape and have this shape prior to insertion into the nostril. The shape of the device is substantially retained during insertion as the INA device is made from a material that is flexible but not highly compressible as described below.

For one embodiment of the invention the anatomically conforming protrusions 107b and 108a help to reduce impediments to the flow of ambient air at ambient pressure. For one such embodiment, anatomically conforming protrusions 107b and 108a reduce the likelihood of typical negative inspiratory pressure progressing to the point of constricting the body's airway. The anatomically conforming protrusions 107b and 108a also help to retain the INA device in-place during use.

Figure 2:
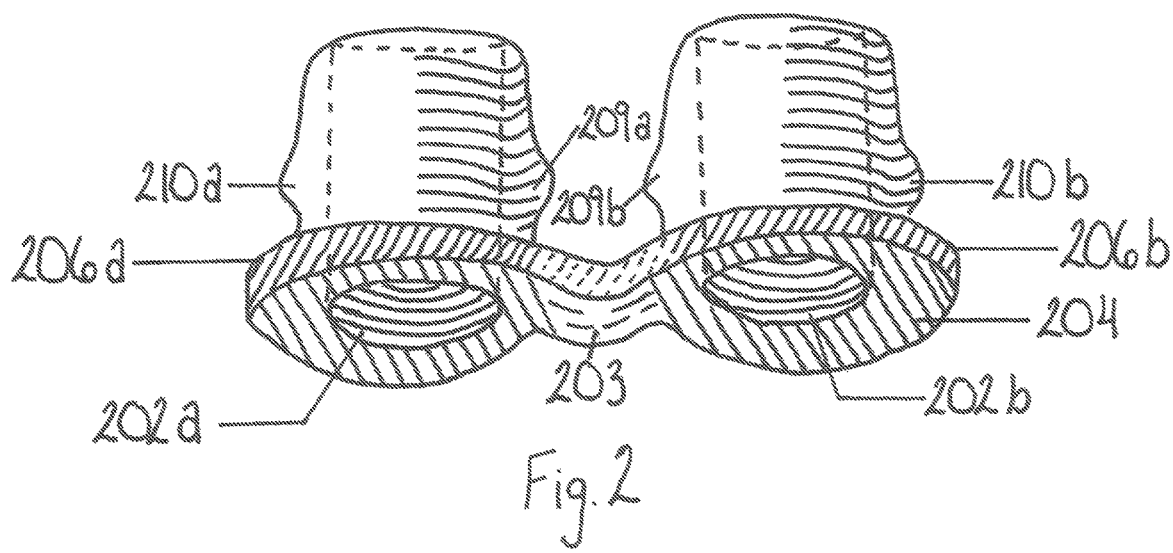
FIG. 2 illustrates an INA device in accordance with one embodiment of the invention.

FIG. 2 illustrates an INA device in accordance with one embodiment of the invention. As shown in FIG. 2, the connecting portion 203 may be curved to accommodate the columella of the user's nose. Also shown in FIG. 2, are additional protrusions 209a and 209b, and 210a and 210b, which engage the user's septum when the INA device has been inserted. The additional protrusions help to retain the device in-place during use. As shown in FIG. 2, septum engaging protrusions 209a and 209b, and 210a and 210b, are relatively small compared to anatomically conforming protrusions 107b and 108a, discussed above, in reference to FIG. 1. For various embodiments, no additional protrusions are included and the INA device is adequately retained with the anatomically conforming protrusions 107b and 108a helping to retain the INA device in-place during use, as discussed above. FIG. 2 also illustrates exterior ends 202a and 202b l of the respective cannulae of the INA device as well as base 204, and lateral flanges 206a and 206b.

Figure 3:
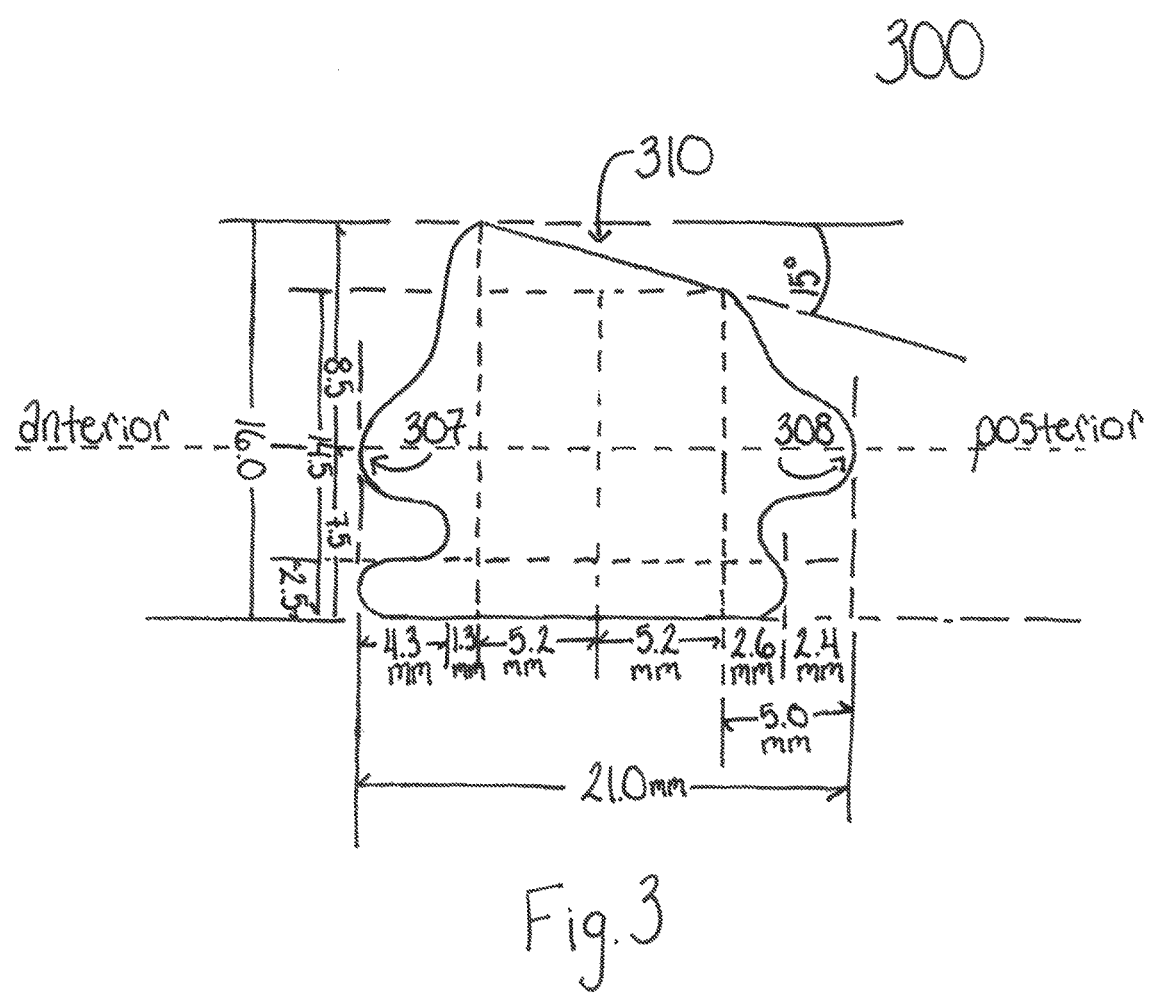
FIG. 3 illustrates a cutaway side view of a cannula of an INA device in accordance with one embodiment of the invention.

FIG. 3 illustrates a cutaway side view of a cannula 300 of an INA device in accordance with one embodiment of the invention. As shown in FIG. 3, the cannula 300 has a nareiform shape. As shown in FIG. 3, the lumen 310 of the cannula 300 has a diameter of 10.4 mm For one embodiment, the cannula may be longer at the anterior end than at the posterior. For example, as shown in FIG. 3, the cannula is approximately 16 mm in length at the anterior end and decreases in length to approximately 14.5 mm at the posterior end, with the top end (insertion end) of the cannula sloping at approximately 15 degrees from the anterior end to the posterior end. As shown in FIG. 3, cannula 300 includes an anterior anatomically conforming protrusion 307 (anterior protrusion 307) that protrudes approximately 5.6 mm from the lumen 310 of cannula 300. The anterior protrusion 307 is positioned on the exterior surface cannula 300 approximately 7.5 mm from the base (i.e. the edge of the base) of cannula 300.

As shown in FIG. 3, cannula 300 also includes a posterior anatomically conforming protrusion 308 (posterior protrusion 308) that protrudes approximately 5 mm from the lumen 310 of cannula 300. The posterior protrusion 308 is also positioned on the exterior surface of cannula 300 approximately 7.5 mm from the base of cannula 300. For various alternative embodiments, the anterior protrusion 307 and the posterior protrusion 308 may be positioned at various distances from the base of the cannula and the distance from the base of the cannula 300 may not be the same for anterior protrusion 307 as for posterior protrusion 308.

Figure 4:
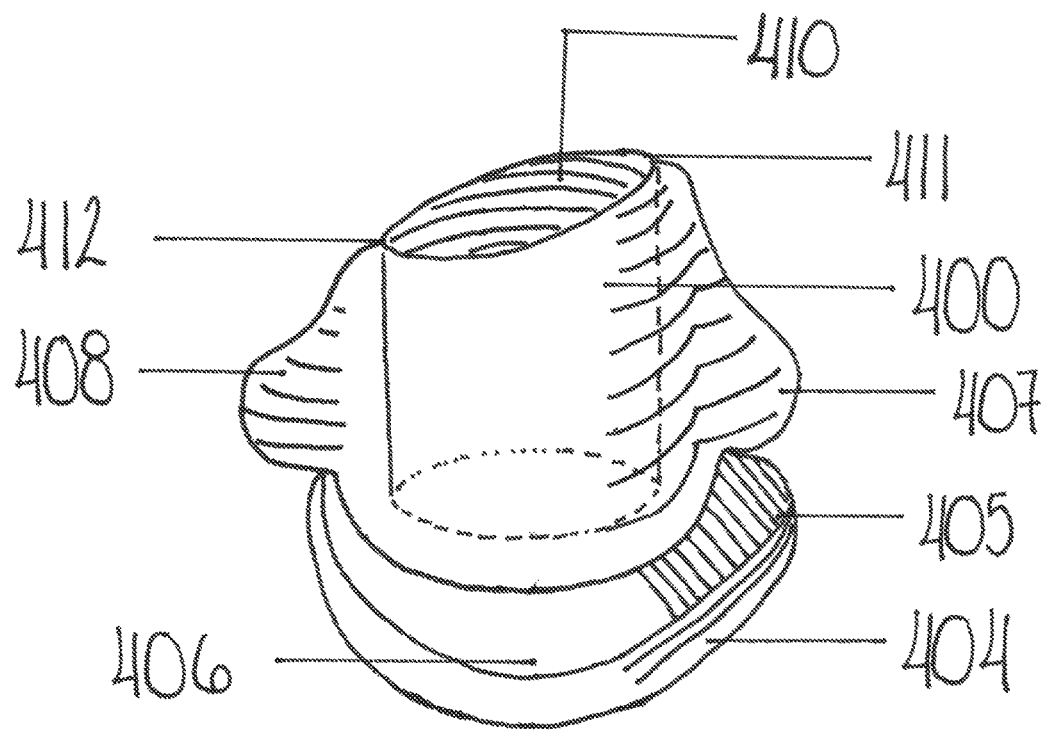
FIG. 4 illustrates a perspective view of a cannula 400 of an INA device in accordance with one embodiment of the invention.

FIG. 4 illustrates a perspective view of a cannula 400 of an INA device in accordance with one embodiment of the invention. As shown in FIG. 4, the cannula 400 has a nareiform shape. As shown in FIG. 4, cannula 400 illustrates a cannula for the right nostril of the user. Cannula 400 has an anterior end 411 that is longer than a posterior end 412, with the cannula 400 sloping from anterior end 411 to posterior end 412, as discussed above in reference to FIG. 3. Cannula 400 also includes a base portion 404 having an anterior flange 405 and a lateral flange 406.

Cannula 400 also includes an anterior protrusion 407 and a posterior protrusion 408. Anterior protrusion 407 and a posterior protrusion 408 are anatomically conforming protrusions that engage, respectively, the anteromedial and posterolateral cul-de-sac concavities of the typical human nose. Anterior protrusion 407 and a posterior protrusion 408 help support the nostrils in an open posture and provide increased airflow.

Figure 5:
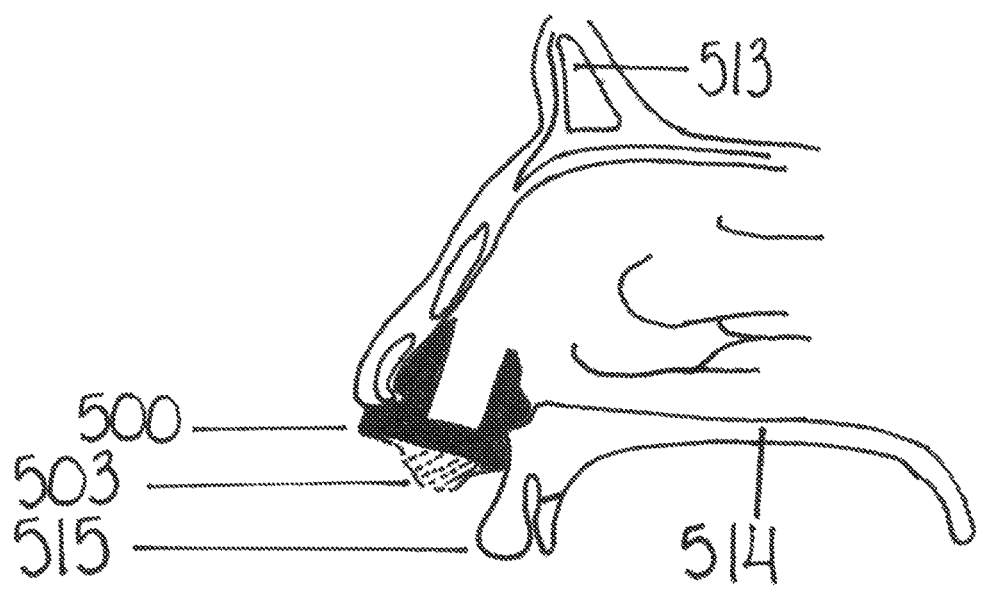
FIG. 5 illustrates a cutaway lateral view of a cannula, in-place, in a right nostril of a user's nose in accordance with one embodiment of the invention.

FIG. 5 illustrates a cutaway lateral view of a cannula 500 in-place in a right nostril of a user's nose in accordance with one embodiment of the invention. As shown in FIG. 5, the cannula 500 has a nareiform shape. As shown in FIG. 5, cannula 500 includes a connecting portion 503. The connecting portion 503 obscures the columella of the user's nose. FIG. 5 illustrates the user's sinus 513, palate 514, and upper lip 515 to reference orientation of the cannula 500 in-place during use. As shown in FIG. 5, the anterior protrusion and the posterior protrusion (not referenced) engage, respectively, the anteromedial and posterolateral cul-de-sac concavities of the typical human nose (not referenced), to help support the nostrils in an open posture and provide increased airflow. As shown in FIG. 5, the cannula has substantially retained a nareiform shape while in-place in the user's nostril.

General Matters

Embodiments of the invention provide an INA device for use in a variety of settings in which increased or improved nasal airflow is desired.

Although embodiments of the invention have been generally described above, various alternative embodiments are possible. For example, although an embodiment of the invention is described above as including an anterior protrusion and a posterior protrusion, alternative embodiments may have only one or the other of such protrusions. Further, although an embodiment of the invention is described above as including a base portion having anterior and lateral flanges, alternative embodiments may have only one or the other of such flanges or no flanges. Additionally, embodiments may include only one cannula, for use in one nostril. For such an embodiment, the connecting portion or bridge may not be required. In alternative embodiments, a cannula in accordance with an embodiment of the invention may be used in conjunction with nasal delivery systems for medication or oxygen. For example, such nasal delivery systems typically include a nosepiece for insertion into a nostril of a user with a substance supply unit connected to the nosepiece, and a delivery mechanism for delivering a substance contained in the substance supply unit to the nostril of the user via the nosepiece. For one embodiment of the invention, the nosepiece of a system includes a cannula having an interior surface defining a generally cylindrical lumen and an exterior surface having one or more anatomically conforming protrusions as discussed above in reference to alternative embodiments of the invention. For such embodiments, the cannula in accordance with such an embodiment may be employed to increase nasal airflow to improve delivery of the medication, oxygen, or other substance delivered intra-nasally.

For one embodiment, the INA device may be constructed of a single material such as, for example, a biologically inert isomer of silicone, urethane, Krayton, or Silastic. For alternative embodiments, the INA device may be constructed from one or more other suitable materials and may be constructed from multiple components. Whatever suitable material is used, the material has the ability to withstand the pressure exerted by insertion into the human nostril without deforming as may be the case with other devices. Therefore, the INA device substantially retains its nareiform shape while in use.

In accordance with one embodiment, an intranasal airway device is constructed of silicone rubber. The intranasal airway device is constructed with an exterior surface having the shape of the human nasal cavity. The intranasal airway device has two cannulae each of which has an interior surface defining a generally cylindrical lumen and an exterior surface having a nareiform shape defined by a first protrusion having the shape of an anteromedial concavity of the human nose and a second protrusion having the shape of a posterolateral concavity of the human nose.

While the invention has been described in terms of several embodiments, those skilled in the art will recognize that the invention is not limited to the embodiments described, but can be practiced with modification and alteration within the spirit and scope of the appended claims. The description is thus to be regarded as illustrative instead of limiting.

What is claimed is:

1. An intranasal device comprising:
a first cannula for insertion into a first nostril of a user;
a second cannula for insertion into a second nostril of a user;
each of the first cannula and the second cannula having an interior surface defining a generally cylindrical lumen and an exterior surface having only one of either a first protrusion or a second protrusion, the first protrusion configured to have a shape of an anteromedial concavity of each of the first nostril and the second nostril, the second protrusion configured to have a shape of a posterolateral concavity of each of the first nostril and the second nostril, wherein the first protrusion and the second protrusion do not form a uniform protrusion around each of the first cannula and the second cannula and wherein the first protrusion is configured to have the shape of the anteromedial concavity and second protrusion is configured to have the shape of the posterolateral concavity prior to insertion into the first nostril and the second nostril of the user.

2. The intranasal device of claim 1 wherein the first cannula and the second cannula are formed as single article of manufacture from a semi-rigid material such that the shapes of the first protrusions and the second protrusions are substantially maintained when each of the first cannula and the second cannula are inserted into the first nostril and the second nostril, respectively.

3. The intranasal device of claim 2 wherein the semi-rigid material is silicone rubber.

4. The intranasal device of claim 2 wherein each of the first cannula and the second cannula have a supporting base, each supporting base having an anterior flange and a lateral flange.

5. The intranasal device of claim 1 further comprising:
a connecting portion, the connecting portion connecting the first cannula to the second cannula.

* * * * *